US00PP33869P2

(12) United States Plant Patent
NeSmith

(10) Patent No.: US PP33,869 P2
(45) Date of Patent: Jan. 18, 2022

(54) SOUTHERN HIGHBUSH BLUEBERRY PLANT NAMED 'TH-889'

(50) Latin Name: *Vaccinium corymbosum*
Varietal Denomination: TH-889

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/229,482

(22) Filed: Apr. 13, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Thomas Horstemeyer, LLP

(57) ABSTRACT

A new and distinct cultivar of *Vaccinium* plant named 'TH-889', characterized by a combination of later season flowering and ripening; large berries with unique, vibrant light blue color and good flavor and firmness; vigorous growth; compact form; attractive fall foliage color; and a chilling requirement of about 500-600 hours below about 45° F.

6 Drawing Sheets

Botanical designation: *Vaccinium corymbosum.*
Cultivar denomination: 'TH-889'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-889'.

The new *Vaccinium corymbosum* 'TH-889' was first identified in 2005 in Griffin, Ga. The new variety 'TH-889' is late season, ripening later than some early commercial varies in south and middle Georgia and has moderately vigorous growth and compact form making it well-suited for home gardens. 'TH-889' has medium to large berries with good scar, good flavor, and distinct light blue color, and a chilling requirement of about 500-600 hours below about 45° F. The new variety 'TH-889' also has multi-season appeal as a home garden plant with attractive fall foliage color, attractive flowering, and vibrant light blue fruit color.

'TH-889' is a product of a cross of 'TH-622' X 'Bluecrisp' made by D. Scott NeSmith in 2002. 'TH-622' is a non-patented breeding line, and 'Bluecrisp' is a patented variety (U.S. Plant Pat. No. 11,033). The new blueberry plant variety 'TH-889' has been tested in asexually propagated (by vegetative cuttings) plantings in Alapaha, Ga. since 2007 where it was established for testing and comparing to industry standards. 'TH-889' was also observed in a trial in Griffin, Ga. from 2007 through 2014. Observations of the resulting 'TH-889' progeny have shown that the unique features of this new *Vaccinium corymbosum* 'TH-889' are stable and reproduced true to type in successive generations.

SUMMARY OF THE INVENTION

The new *Vaccinium* cultivar 'TH-889' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-889'. In combination, these traits set 'TH-889' apart from all other existing varieties of southern highbush blueberry known to the inventors:

1. late season, flowering and ripening later than early commercial variety 'Rebel' and near the time of 'Camellia' in south and middle Georgia;
2. medium to large fruit with vibrant light blue color and flavor as compared to 'Rebel' and 'Camellia';
3. moderately vigorous growth with compact form well-suited to home gardens;
4. chilling requirement of about 500-600 hours below about 45° F. (based on comparison of flowering dates with those of known standard cultivars);
5. firmer berries compared to 'Camellia' and larger, firmer, sweeter berries compared to 'Rebel'.

Comparison: As compared to the female parent 'TH-622' and male parent 'Bluecrisp', plants of the new *Vaccinium* cultivar 'TH-899' have a chilling requirement of about 500-600 hours, which is similar to 'TH-622' (550 to 600 hours) but higher than 'Bluecrisp' (350 to 450 hours). 'TH-889' flowers and ripens 7 to 10 days later than 'Bluecrisp'. Berry size of 'TH-889' is similar to 'Bluecrisp' (2.0 to 2.4 g/berry) but smaller than 'TH-622' (2.8 to 3.5 g/berry). The most distinguishing trait in which 'TH-889' differs from both parents is the remarkable light blue fruit color it has due to the intense, waxy bloom.

Plants of the new *Vaccinium corymbosum* can also be compared to early season southern highbush blueberry cultivar 'Rebel' (U.S. Plant Pat. No. 18,138) and later variety 'Camellia' (U.S. Plant Pat. No. 18,151). The selection 'TH-889' begins flowering and ripening slightly later than early variety 'Rebel' and near the same time as later variety 'Camellia' in south and middle Georgia. 'TH-889' has medium to large berries with good scar, good flavor, and vibrant light blue color and flavor as compared to 'Camellia' and 'Rebel' at Alapaha and Griffin over a 5-year period (Tables 1 and 2). Plants are moderately vigorous, but compact, making them well suited for home gardeners. No notable diseases or other pest problems have been observed for the new variety that are not also common for other varieties. The new variety is estimated to have a chilling requirement of about 500-600 hours, more or less, below about 45° F. (based on comparison of flowering dates with those of known standard cultivars) when produced under typical low to mid chill production regions. 'TH-889' produces berries firmer than 'Camellia', and larger, firmer, and sweeter than 'Rebel' as apparent from comparisons to those standard varieties in Griffin, Ga. during 2010-2012 (Table 3) . Additional comparison data of 'TH-889' with 'Camellia' and 'Rebel' are presented in the tables below.

The new *Vaccinium* 'TH-889' has multi-season appeal as a home garden plant too, as it typically develops attractive fall foliage color (FIG. 1). The plant is also attractive during flowering (FIG. 2) and fruiting (FIG. 3), with the ripe fruit displaying a novel, vibrant light blue color (FIG. 4).

TABLE 1

5-year average ratings of fruit and plant characteristics of variety 'TH-889' and commercial cultivars 'Camellia'and 'Rebel' from 2009-2013 in field test plots at Alapaha, GA. Rating scales are based on a 1 to 10 score, with 1 being the least desirable and 10 being the most desirable. These plants were established in 2007.

| | Alapaha location | | |
|---|---|---|---|
| Attribute | 'Rebel' | 'Camellia' | 'TH-889' |
| Berry size | 7.7 ± 0.2 | 8.9 ± 0.2 | 7.8 ± 0.2 |
| Berry scar | 7.4 ± 0.2 | 7.2 ± 0.2 | 7.8 ± 0.2 |
| Berry color | 7.2 ± 0.2 | 8.7 ± 0.2 | 9.0 ± 0.2 |
| Berry firmness | 7.8 ± 0.1 | 7.2 ± 0.1 | 7.9 ± 0.2 |
| Berry flavor | 6.7 ± 0.1 | 7.8 ± 0.1 | 7.7 ± 0.2 |
| Cropping | 4.9 ± 1.6 | 5.4 ± 0.3 | 6.4 ± 0.8 |
| Plant vigor | 8.4 ± 0.4 | 9.8 ± 0.2 | 7.9 ± 0.1 |
| Date of 50% flowering | Feb. 24 | Mar. 11 | Mar. 19 |
| Date of 50% ripening | May 3 | May 15 | May 17 |
| Fruit development period (days) | 67.3 ± 4.5 | 65.3 ± 4.9 | 58.6 ± 2.9 |

TABLE 2

5-year average ratings of some fruit and plant characteristics of variety 'TH-889' and commercial cultivars 'Camellia' and 'Rebel' from 2009-2013 in field test plots at Griffin, Ga. Rating scales are based on a 1 to 10 score, with 1 being the least desirable and 10 being the most desirable. These plants were established in 2007.

| | Griffin location | | |
|---|---|---|---|
| Attribute | 'Rebel' | 'Camellia' | 'TH-889' |
| Berry size | 7.5 ± 0.1 | 8.6 ± 0.2 | 7.5 ± 0.2 |
| Berry scar | 7.5 ± 0.1 | 7.0 ± 0.1 | 7.9 ± 0.2 |
| Berry color | 7.2 ± 0.1 | 7.9 ± 0.2 | 8.7 ± 0.2 |
| Berry firmness | 7.4 ± 0.1 | 7.2 ± 0.1 | 7.9 ± 0.2 |
| Berry flavor | 6.6 ± 0.2 | 7.4 ± 0.2 | 7.7 ± 0.2 |
| Cropping | 4.9 ± 1.1 | 7.9 ± 0.2 | 6.0 ± 0.9 |
| Plant vigor | 6.3 ± 0.3 | 9.8 ± 0.1 | 8.1 ± 0.2 |

TABLE 2-continued 5-year average ratings of some fruit and plant characteristics of variety 'TH-889' and commercial cultivars 'Camellia' and 'Rebel' from 2009-2013 in field test plots at Griffin, Ga. Rating scales are based on a 1 to 10 score, with 1 being the least desirable and 10 being the most desirable. These plants were established in 2007.

| | Griffin location | | |
|---|---|---|---|
| Attribute | 'Rebel' | 'Camellia' | 'TH-889' |
| Date of 50% flowering | Mar. 8 | Mar. 25 | Mar. 27 |
| Date of 50% ripening | May 12 | May 31 | May 27 |
| Fruit development period (days) | 65.2 ± 7.5 | 67.3 ± 4.8 | 60.8 ± 2.1 |

TABLE 3

Berry weight, firmness, and Brix for two commercial southern highbush blueberry cultivars 'Rebel and 'Camellia' and 'TH-889' grown in Griffin, GA during 2010-2013.

| Selection or cultivar | Berry weight (g/25 fruit) | Berry firmness (g/mm) | Berry Brix (%) |
|---|---|---|---|
| Rebel | 46.1 ± 9.9 | 180 ± 5.4 | 11.9 ± 0.5 |
| Camellia | 54.2 ± 9.3 | 168 ± 5.0 | 13.9 ± 0.4 |
| TH-889 | 52.6 ± 3.6 | 193 ± 2.9 | 13.1 ± 0.5 |

BRIEF DESCRIPTION OF THE DRAWINGS

The accompanying colored photographic illustrations show the overall appearance and distinct characteristics of the new cultivar of *Vaccinium corymbosum* 'TH-889' showing the colors as true as possible. Colors in the photographs may differ slightly from the color values cited in the detailed botanical description, which accurately describes the colors of the new *Vaccinium corymbosum* 'TH-889'. Photographs were taken of plants grown outdoors in Alapaha, Ga. and Griffin, Ga. during different years.

The photographs labeled

The photograph labeled

The photograph labeled

The photograph labeled

The photographs labeled

The photographs labeled

DETAILED BOTANICAL DESCRIPTION

Figure 1A:
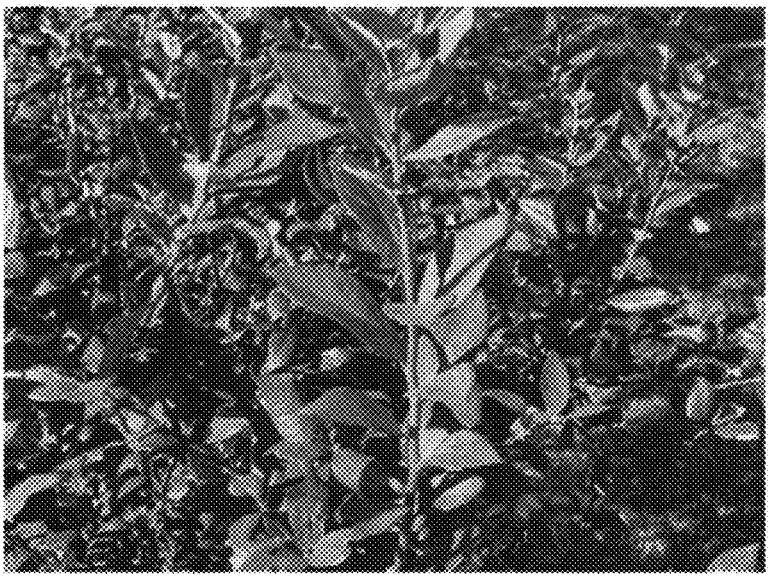
FIGS. 1A and 1B depict typical 4-year old 'TH-889' plants during autumn showing fall foliage color, with FIG. 1A showing a close up view of branches of a 'TH-889' plant and FIG. 1B showing a row of several 'TH-889' plants. Photographs were taken in October 2011 in Griffin, Ga.
Figure 1B:
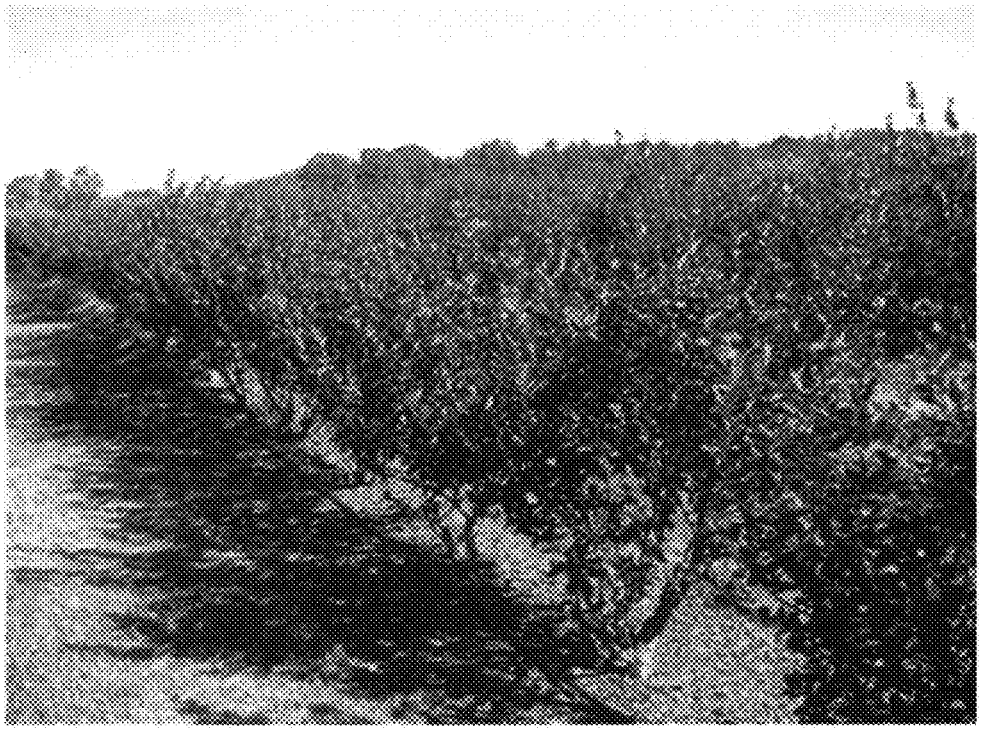
Figure 2:
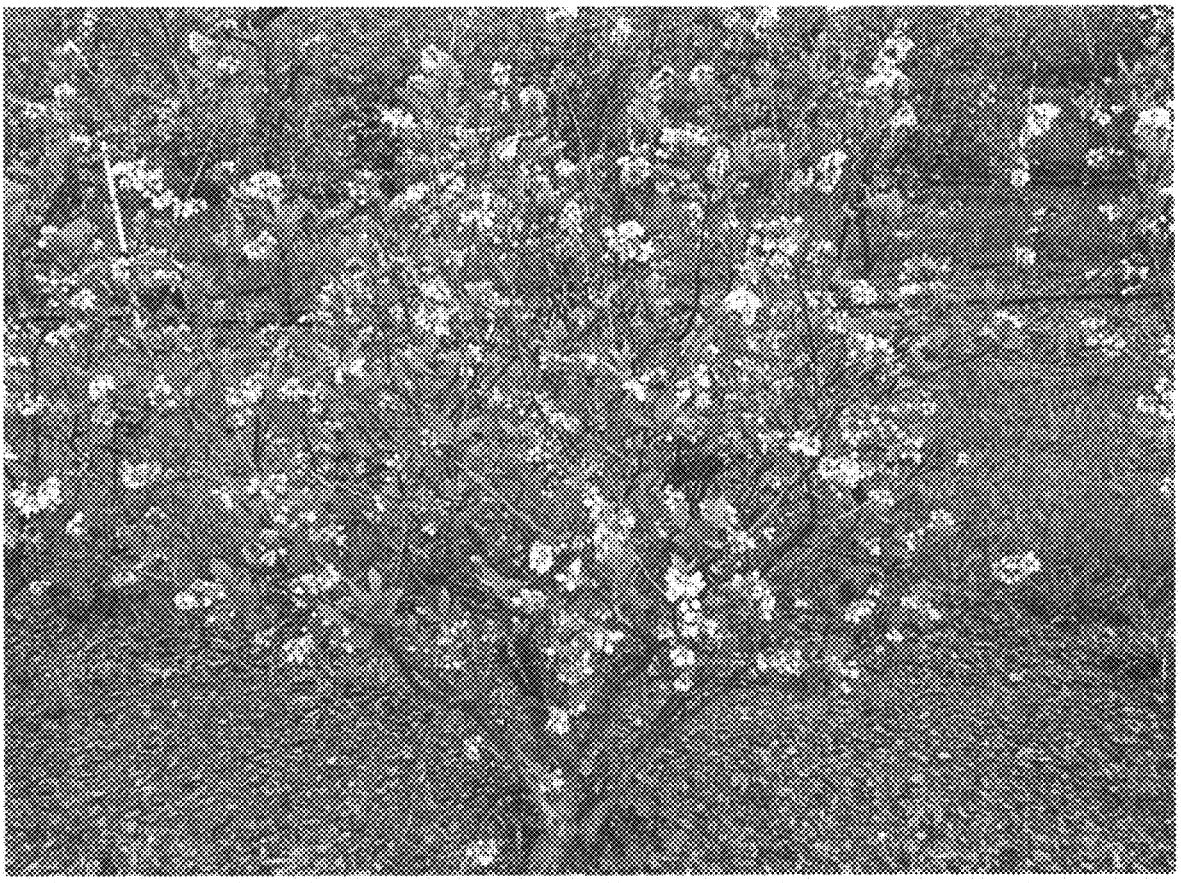
FIG. 2 depicts a typical 5-year old 'TH-889' plant during flowering in Griffin, Ga., taken in March 2012.
Figure 3:
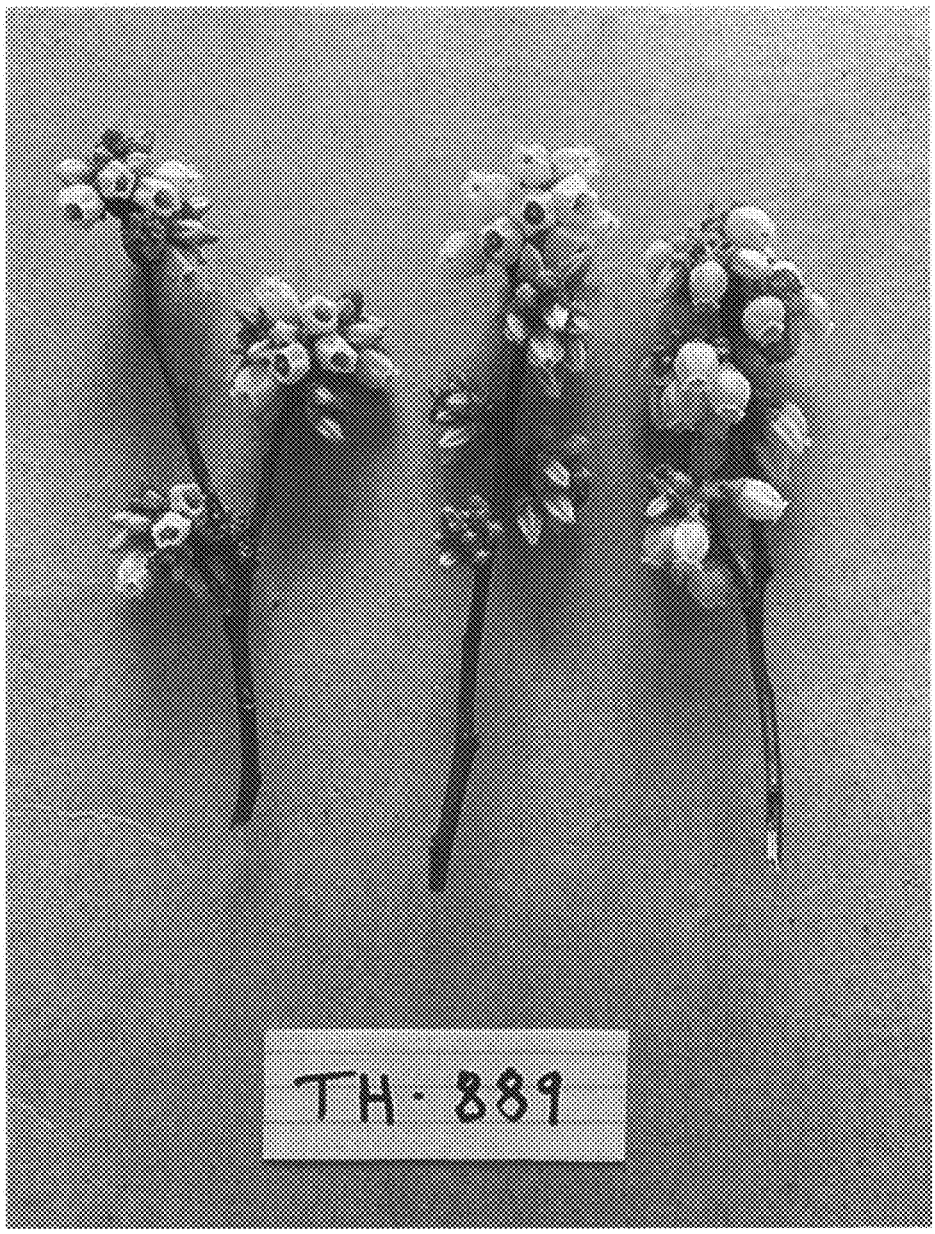
FIG. 3 depicts a close-up view of flowering branches of a 'TH-889' plant.
Figure 4:
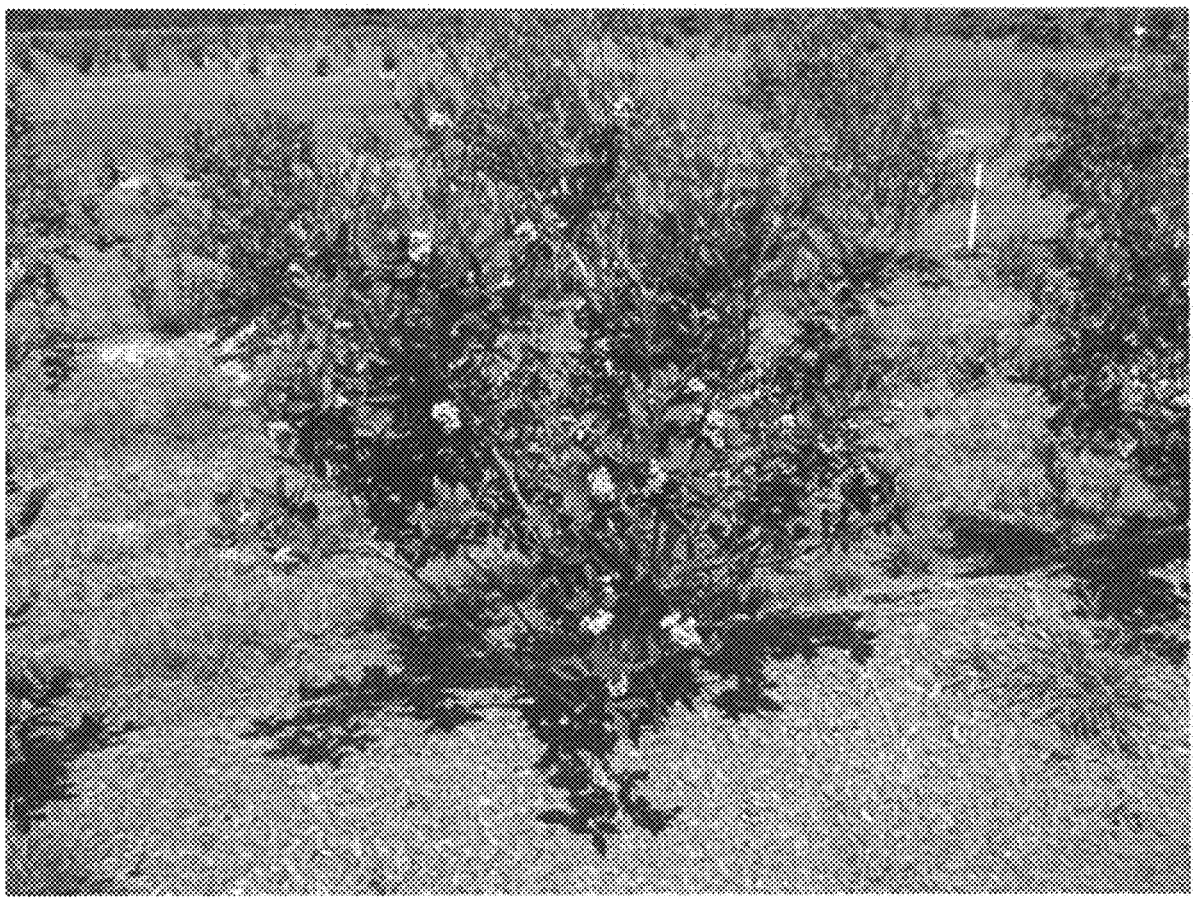
FIG. 4 depicts typical 4-year old plants of 'TH-889' during fruit ripening, taken in Alapaha, Ga. in May 2011.
Figure 5A:
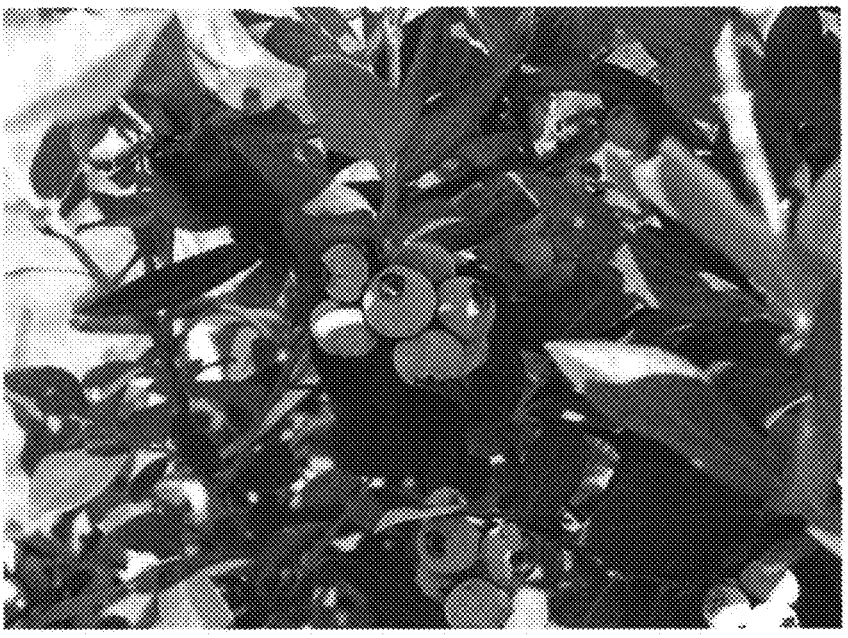
FIGS. 5A and 5B depict close-up views of maturing fruit of 'TH-889' showing the unique, vibrant light-blue fruit color, taken in May 2011.
Figure 5B:
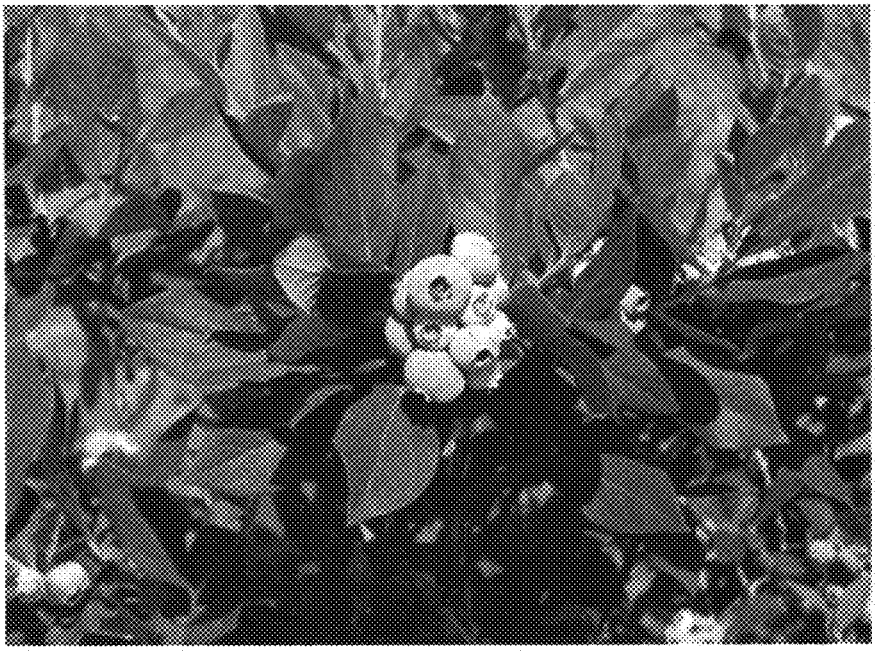
Figure 6A:
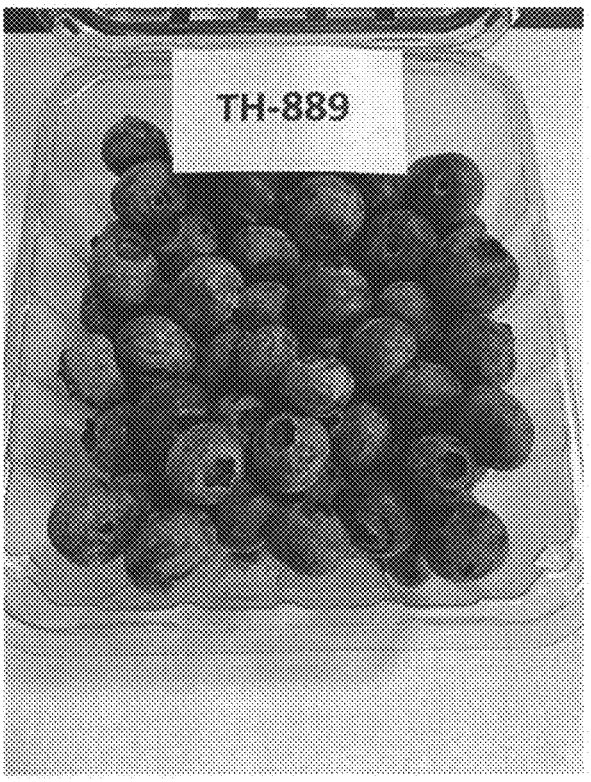
FIG. 6A and FIG. 6B are close-up views of ripe fruit of 'TH-889', with FIG. 6B depicting two sliced berries to reveal the inside of the fruit.
Figure 6B:
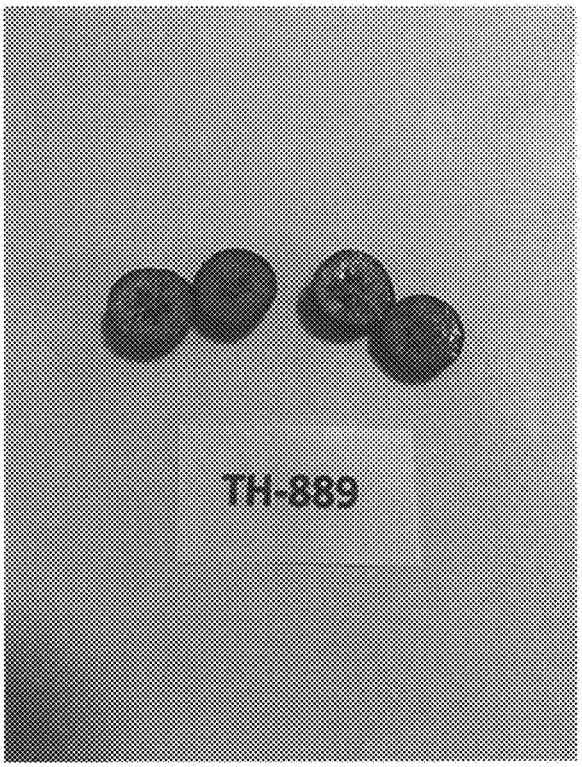

The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TH-889'.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-889'. Where dimensions, sizes, colors, and other characteristics are given, it is to be understood that such characteristics are approximations and averages set forth as accurately as practicable. Data were collected between the years of 2009-2013 from horticulture farms and nurseries in Alapaha and/or Griffin, Ga. from 4 to 6-year-old plants (planted in the field with supplemental irrigation). The average low temperature for the year ranges from about 54° F. to 58° F., and the average high temperature for the year ranges from about 78° F. to 82° F.

Botanical classification: *Vaccinium corymbosum* 'TH-889'.

*Commercial classification*.—Fruit-bearing shrub.

*Parentage*.—'TH-622' (non-patented breeding line) and 'Bluecrisp' (U.S. Plant Pat. No. 11,033).

Growth and propagation:

*Propagation type*.—Vegetative by softwood cuttings.

*Growth rate*.—Moderately vigorous and semi-compact.

*Root description*.—Fibrous.

Plant description:

*Growth habit*.—Plant is semi-spreading, with about 1 to 3 main canes arising from the crown, and multiple branching of shoots from those canes about 10 to 15 cm above ground.

*Usage*.—Home gardens and/or commercial fruit production.

*Productivity*.—Medium to high crop/yield. Yields of about 6 to 9 lbs per plant each year on plants around 4 years old or older grown under well fertilized and irrigated field conditions.

*Size of plant*.—Plant is about 1.2 to 1.4 m tall by about 3 years. The plant crown, or base, is narrow, typically about 10 to 15 cm in diameter. Upper portion of plant canopy reaches about 1.1 to 1.3 m in diameter by about 3 to 4 years.

*Cold hardiness*.—Similar to mid-season southern highbush varieties such as 'Camellia' (U.S. Plant Pat. No. 18,151).

*Disease resistance*.—No exceptional disease resistance or susceptibility observed. Typical for southern highbush such as 'Camellia' and 'Rebel'.

*Chilling requirement*.—Plants are medium chill, requiring only about 500 to 600 hours, more or less, of temperatures at or below about 7° C. to induce normal leafing and flowering. The chill requirement is more than the male parent 'Bluecrisp' (U.S. Plant Pat. No. 11,033; 300 to 400 hours of chilling required), and similar to the female parent 'TH-622' (non-patented breeding selection; 500 to 600 hours of chilling required).

*Leafing*.—Plants tend to break sufficient leaf buds simultaneously with, or shortly after, anthesis.

*Canes*.—Main cane base diameter about 25 to 40 mm, color most near Brown N 200D to Grey 201B; two year old cane diameter about 10 to 15 mm, color transitioning from Yellow Green 145C to Greyed Orange 165A and 166B; current season wood diameter about 5 to 10 mm, color Yellow Green 145C.

*Fruiting wood*.—Moderate number of twigs of about 10 to 15 cm in length, with internode lengths of about 10 to 20 mm common.

Foliage:

*Leaf color*.—Healthy mature leaves: top side of leaf color is Green 137B, under side of leaf color is Green N138C.

*Leaf arrangement*.—Alternate, simple.

*Leaf shape*.—Elliptic.

*Leaf margins*.—Entire.

*Leaf venation*.—Pinnate slightly to moderately reticulated.

*Leaf apices*.—Broadly acute.

*Leaf bases*.—Acute.

*Leaf dimensions*.—Length: about 60 to 75 mm; width: about 30 to 40 mm.

*Petioles*.—Small, about 3.5 to 4.5 mm long, about 1.5 to 2.0 mm wide; Color: Yellow Green 145C.

*Texture*.—Leaf margins, smooth; both upper and lower leaf surfaces, glaucous.

Flowers:

*Date of* 50% *anthesis*.—5-year average March 19 in south Georgia; March 27 in middle Georgia.

*Flower shape*.—Urceolate.

*Flower bud number*.—High, averaging 4 to 5 buds per fruiting shoot.

*Flowers per cluster*.—7 to 10 common.

*Flower fragrance*.—Slight cut flower fragrance.

*Corolla color*.—White 155C.

*Corolla length*.—About 9.0 to 10.0 mm.

*Corolla width*.—About 6.0 to 7.0 mm.

*Corolla aperture width*.—About 3.0 to 3.5 mm.

*Flower peduncle*.—Length about 7.0 to 9.0 mm; Color: Green 138D.

*Flower pedicel*.—Length about 4.0 to 5.0 mm; Color: Green 138D.

*Calyx* (*with sepals*).—Diameter: about 6.5 to 7.5 mm; Color: Green 138C.

*Stamen*.—Length: about 6.5 to 7.7 mm; number per flower: about 10; filament color: Green White 157D.

*Style*.—Length: about 8.0 to 10.0 mm; Color: Yellow Green 145B.

*Pistil*.—Length: about 9.0 to 11.0 mm; ovary color: Green 138C.

*Anther*.—Length: about 4.0 to 5.0 mm; number: 10; Color: Greyed Orange 165B to 165C.

*Pollen*.—Abundance: low to medium; Color: White 155A to 155B.

*Compatibility*.—The cultivar has a moderate degree of self-compatibility.

Fruit:

*Date of* 50% *maturity*.—5-year average May 17 in south Georgia and May 27 in middle Georgia.

*Fruit development period*.—About 58 to 61 days.

*Berry color*.—With wax Violet Blue 97C to Blue 100D; with wax removed Black 203A.

*Berry flesh color*.—Green White 157B.

*Berry surface wax abundance*.—Very high.

*Berry weight*.—1st harvest: about 2.2 to 2.5 g; 2nd harvest: about 1.7 to 2.0 g.

*Berry size*.—Height from calyx to scar: about 13 to 15 mm; diameter: about 15 to 17 mm.

*Berry shape*.—Semi-spherical to semi-disk shape.

*Fruit stem scar*.—Small to medium, dry, with no tearing upon harvest.

*Calyx*.—Depth shallow, about 1.5 to 2.5 mm; width medium, about 5.0 to 7.0 mm; sepals usually present, semi-erect or inward when present, about 1.0 to 1.5 mm.

*Berry firmness*.—Very good.

*Berry flavor and texture*.—Semi-sweet, mild acidic flavor; slightly crisp; smooth texture.

*Storage quality*.—Very good.

*Suitability for mechanical harvesting*.—Not likely suitable.

*Uses*.—Intended for home gardens, but also likely suitable for commercial production in some areas.

Seed:

*Seed abundance in fruit*.—Medium, about 10 to 20 fully developed seeds per berry.

*Seed color*.—Greyed Orange 164B to 165B.

*Seed dry weight*.—About 55.2 mg per 100 seed.

*Seed size*.—About 1.4 to 2.0 mm long.

It is claimed:

1. A new and distinct cultivar of the *Vaccinium* plant named 'TH-889' as illustrated and described herein.

* * * * *